United States Patent
Pant et al.

(10) Patent No.: US 6,740,337 B2
(45) Date of Patent: May 25, 2004

(54) BIOAVAILABLE DOSAGE FORM OF ISOTRETINOIN

(75) Inventors: Abha Pant, Plainsboro, NJ (US); Inderdeep Bhatia, New Delhi (IN); Sunilendu Bhushan Roy, Indore (IN); Rajiv Malik, New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/829,246

(22) Filed: Apr. 9, 2001

(65) Prior Publication Data

US 2002/0025338 A1 Feb. 28, 2002

(30) Foreign Application Priority Data

Jun. 16, 2000 (IN) ...................................... 596/DEL/2000

(51) Int. Cl.$^7$ .................. A61K 9/14; A61K 31/445; A61K 9/48
(52) U.S. Cl. .................. 424/451; 424/489; 514/317
(58) Field of Search .................. 514/317; 424/489, 424/451

(56) References Cited

U.S. PATENT DOCUMENTS

| | | | |
|---|---|---|---|
| 4,016,254 A | * 4/1977 | Seager | 424/497 |
| 4,808,630 A | 2/1989 | Straw | 514/317 |
| 6,045,829 A | * 4/2000 | Liversidge et al. | 424/489 |
| 6,284,283 B1 | * 9/2001 | Costantino et al. | 264/4.1 |

FOREIGN PATENT DOCUMENTS

WO   WO 00/25772   1/1988

OTHER PUBLICATIONS 1987 edition of the Physicians Desk Reference, p. 1641.*

* cited by examiner

Primary Examiner—Thurman K. Page
Assistant Examiner—Retford Berko
(74) Attorney, Agent, or Firm—Jayadeep R. Deshmukh, Esq.

(57) ABSTRACT

The present invention relates to a bioavailable pharmaceutical composition of 13-cis vitamin A acid (also known as 13-cis retinoic acid and isotretinoin) and a process for preparing the same. 13-cis vitamin A acid is a relatively water insoluble compound that degrades when exposed to light and atmospheric oxygen. Due to its instability and relative insolubility, the bioavailability of the drug after oral administration is difficult to achieve and has always been a challenge to a development pharmacist. It would therefore be desirable to provide a dosage form in which the drug is stable and predictably bioavailable.

21 Claims, No Drawings

BIOAVAILABLE DOSAGE FORM OF ISOTRETINOIN

FIELD OF THE INVENTION

The present invention relates to a bioavailable pharmaceutical composition of 13-cis vitamin A acid (also known as 13-cis retinoic acid and isotretinoin) and a process for preparing the same. 13-cis vitamin A acid is a relatively water insoluble compound that degrades when exposed to light and atmospheric oxygen. Due to its instability and relative insolubility, the bioavailability of the drug after oral administration is difficult to achieve and has always been a challenge to a development pharmacist. It would therefore be desirable to provide a dosage form in which the drug is stable and predictably bioavailable.

BACKGROUND OF THE INVENTION

U.S. Pat. No. 4,464,394 assigned to Hoffman LaRoche Inc. discloses compositions and methods of using 13-cis vitamin A acid against the development of epithelial carcinomas of the skin, gastrointestinal tract, respiratory tract or genito-urinary tract. However, only a general description of the composition is given in this patent and no data on the bioavailability of the active ingredient in the composition is disclosed.

European Patent No. 184942 assigned to Ortho Pharmaceutical Corp. discloses pharmaceutical compositions having not more than 22% wax content which is a critical limitation of this patent, as higher wax content tends to diminish the bioavailability. The particle size of the drug is also reduced to less than 12 $\mu$m prior to its incorporation into the formulation. Said objectives of the bioavailability are achieved by controlling the particle size and the wax content. As 13-cis vitamin A may cause decreased night vision and corneal opacities at higher concentrations, its micronization in the powder state can be hazardous as this involves a lot of dry powder handling. Further, handling of isotretinoin at room temperature under atmospheric oxygen can lead to its degradation, as it is a highly unstable drug.

SUMMARY OF THE INVENTION

It is an object of the present invention to solve the problems associated with the prior art and to provide a process which uses conditions that are convenient to perform on a commercial scale and are operationally safe.

More particularly, the present invention relates to a process of making bioavailable capsule formulation of 13-cis vitamin A acid comprising the steps of (a) mixing the drug with the carrier to form the medicament paste (b) milling the medicament paste to achieve a particle size less than 300 $\mu$m, and (c) mixing the milled medicament paste with the suspending agent, and optionally with carrier material and other pharmaceutically acceptable excipients.

It is observed that the particle size is critical in achieving the bioequivalence against the commercially available marketed formulation of isotretinoin sold under the trade name of "Accutane". In preferred embodiments of the invention, the particle size of 13-cis vitamin A acid in the medicament paste is less than 275 $\mu$m. The surface area of the drug in the medicament paste varies between 0.05–0.3 sq m/g. The medicated paste is milled using any of the conventionally known techniques, such as ball mill, colloid mill etc.

The carrier material used in accordance with the present invention may be selected from the group consisting of peanut oil, soyabean oil, sesame oil, mineral oil, cotton seed oil, polyethylene glycol and mixtures thereof.

The suspending agent used in accordance with the present invention is a wax mixture comprising 1 part hydrogenated soyabean oil, 1.2 parts white wax and 4.2 parts hydrogenated vegetable oil. The suspending agent is used in amounts of more than 30% of the formulation. More preferably, the suspending agent is used in amounts between 30–40% w/w of the formulation.

The formulation of the present invention may further contain suitable pharmaceutical excipients such as anti-oxidants and chelating agents.

The anti-oxidant employed in the present invention may be selected from the group consisting of $\alpha$-tocopherol, butylated hydroxyanisole (BHA), butylated hydroxytoluene (BHT), ascorbyl palmitate and propyl gallate. Chelating agents may be chosen amongst disodium edetate and calcium disodium edetate.

Investigations were conducted in order to determine the effect of particle size on the bioavailability of 13-cis vitamin A acid in the formulations of this invention. The blood levels of the drug were compared with that of the commercially available formulation of 13-cis vitamin A acid sold as a soft gelatin capsule, under the trade name of "Accutane". The area under the plasma concentration (13-cis vitamin A acid) vs. time curve (AUC) was determined between time "0" and time "t" to give the $AUC_{(0-t)}$ values and was then extrapolated to infinity ($\infty$) to calculate the value till there was no more drug in the plasma. This value is reported as $AUC_{(0-\infty)}$. The maximum plasma concentration (Cmax) was also determined for each subject after each treatment.

DETAILED DESCRIPTION OF THE INVENTION

The following examples further illustrate the invention but are not intended to limit the scope of the invention. Soft gelatin capsules were prepared as described in Table 1.

TABLE 1

| | Amount (mg) |
|---|---|
| Isotretinoin | 40 |
| Wax mixture* | 97.86 |
| Butylated hydroxytoluene | 0.032 |
| Disodium edetate | 0.160 |
| Soyabean oil | 181.0 |
| Total | 320.0 |

*The wax mixture was composed of hydrogenated soyabean oil, white wax and hydrogenated vegetable oil in the ratio of 1:1.2:4.2.

Isotretinoin was mixed with soyabean oil to form a 25% dispersion or medicated paste. The medicated paste was milled and the particle size of the drug in the paste following milling was determined. The remaining amount of the carrier material (soyabean oil), wax mixture and other ingredients were then added to the milled medicated paste and mixed with stirring. The formulation so prepared was used to study the effect of particle size on the bioavailability of the drug keeping all the other formulation parameters constant.

EXAMPLE 1

The particle size of the drug in the medicated paste was 90% less than 240 $\mu$m and 50% less than 118 $\mu$m. The surface area of the drug in the paste varied between 0.06–0.13 sq m/g.

This formulation was subjected to a two way cross over bioequivalence study with Accutane (which was the reference product). Seventeen normal, male subjects were enrolled in each study. Whole blood samples were drawn at selected times following each treatment. Blood levels of the drug for both test and reference were determined and compared for the two critical parameters of AUC and Cmax. (Table 1.1). Test is the formulation made according to the present invention and reference is the formulation of 13-cis Vitamin A acid sold under the trade name of "Accutane".

TABLE 1.1

|  | $AUC_{(0-t)}$ | $AUC_{(0-\infty)}$ | Cmax ($\mu$g/ml) |
|---|---|---|---|
| Test/Reference (%) | 110 | 108 | 107.8 |

EXAMPLE 2

Keeping all the other parameters constant, the average particle size of the drug in the medicated paste was increased to 90% below 276 $\mu$m and 50% below 169 $\mu$m and its surface area was between 0.05–0.18 sq. m/g.

This formulation was subjected to a bioequivalence study on 19 healthy, male subjects. Blood samples were drawn at selected intervals following each treatment, the plasma samples were assayed for 13-cis Vitamin A acid to determine the AUC and Cmax as compared to "Accutane". The results are shown in Table 2.1.

TABLE 2.1

|  | $AUC_{(0-t)}$ | $AUC_{(0-\infty)}$ | Cmax ($\mu$g/ml) |
|---|---|---|---|
| Test/Reference (%) | 76.72 | 80.60 | 84.64 |

EXAMPLE 3

In the next experiment the particle size was reduced to study its effect on the bioavailability of the drug when compared with "Accutane". The particle size of the drug in the medicated paste was reduced to 90% below 131 $\mu$m and 50% below 52.4 $\mu$m. The surface area was around 0.20 sq. m/g.

Bioequivalence study was carried on 19 healthy male subjects and the test/reference ratios for AUC and Cmax were compared with Accutane as the reference product.

TABLE 3.1

|  | $AUC_{(0-t)}$ | $AUC_{(0-\infty)}$ | Cmax ($\mu$g/ml) |
|---|---|---|---|
| Test/Reference (%) | 124.5 | 126.8 | 127.0 |

EXAMPLE 4

The particle size of the drug in the medicated paste was 90% less than 225 $\mu$m and 50% less than 110 $\mu$m. The particle size was between 0.09 to 0.11 sq m/g. The effect of this particle size on the bioavailability of the drug was determined as described in Example 1 and the test reference ratios were compared with Accutane as the reference product (Table 4.1).

TABLE 4.1

|  | $AUC_{(0-t)}$ | $AUC_{(0-\infty)}$ | Cmax ($\mu$g/ml) |
|---|---|---|---|
| Test/Reference (%) | 91.5 | 92.7 | 94.0 |

While the present invention has been described in terms of its specific embodiments, certain modifications and equivalents will be apparent to those skilled in the art and are intended to be included within the scope of the present invention.

We claim:

1. A bioavailable capsule formulation of 13-cis Vitamin A acid particles said formulation comprising:
   (a) a medicament paste of 13-cis Vitamin A acid particles and a carrier, wherein 90% of said particles have a size of less than 240 $\mu$m and 50% of said acid particles have a size of less than 118$\mu$m, and wherein the surface area of said acid particles is between 0.05–0.3sq.m/g.
   (b) a suspending agent comprising more than 30 percent by weight of the formulation, and other pharmaceutically acceptable excipients.

2. The formulation of claim 1 wherein 90% of said acid particles have a size of less than 131 $\mu$m and 50% of said acid particles have a size of less than 52 $\mu$m.

3. The formulation of claim 1 wherein the particle size of the acid is less than 275 $\mu$m.

4. The formulation of claim 1 wherein the carrier is selected from the group consisting of peanut oil, soybean oil, sesame oil, mineral oil, cotton seed oil and polethylene glycol.

5. The formulation of claim 1 wherein the suspending agent is a wax mixture comprising 1 part hydrogenated soyabean oil, 1.2 parts white wax and 4.2 parts hydrogenated vegetable oil.

6. The formulation of claim 1 wherein the suspending agent is 30–40 percent by weight of the formulation.

7. The formulation of claim 1 wherein the dosage form may contain other pharmaceutically acceptable excipients such as chelating agents and anti-oxidants.

8. The formulation of claim 7 wherein the chelating agent is selected from amongst disodium edetate and calcium disodium edetate.

9. The formulation of claim 7 wherein the anti-oxidants are selected from the group consisting α-tocopherols, butylated hydroxyanisole, butylated hydroxytoluene, ascorbyl palmitate and propyl gallate.

10. The formulation of claim 1 wherein the drug in the medicament paste is milled by conventional techniques such as ball mill or colloid mill.

11. A process for the preparation of a bioavailable capsule formation of 13-cis vitamin A acid comprising the steps of:
    (a) mixing particles of the acid with the carrier to form a medicament paste;
    (b) milling the medicament paste to achieve a particle size of said acid of less 90% less than about 240 $\mu$m and 50% less than about 118 $\mu$m; and wherein the surface area of said particles is between 0.05–0.3 sq. m/g; and
    (c) mixing the milled medicated paste with a suspending agent and other pharmaceutically acceptable excipients.

12. The process of claim 11 wherein 90% of said acid particles have a size of less than 131 $\mu$m and 50% of said acid particles have a size of less than 52 $\mu$m.

13. The process of claim 11 wherein the particle size of the acid is less than 275 μm.

14. The process of claim 11 wherein the carrier is selected from the group consisting of peanut oil, soyabean oil, sesame oil, mineral oil, cotton seed oil and polyethylene glycol.

15. The process of claim 11 wherein the suspending agent is a wax mixture comprising 1 part hydrogenated soyabean oil, 1.2 parts white wax and 4.2 parts hydrogenated vegetable oil.

16. The process of claim 15 comprising more than 30 weight percent of the suspending agent.

17. The process of claim 16 wherein the suspending agent is between 30–40 weight percent.

18. The process of claim 11 wherein the dosage form may contain other pharmaceutically acceptable excipients such as chelating agents and anti-oxidants.

19. The process of claim 18 wherein the chelating agent is selected from amongst disodium edetate and calcium disodium edetate.

20. The process of claim 18 wherein the anti-oxidants are selected from the group consisting α-tocopherols, butylated hydroxyanisole, butylated hydroxytoluene, ascorbyl palmitate and propyl gallate.

21. The process of claim 11 wherein the drug in the medicament paste is milled by conventional techniques such as ball mill or colloid mill.

\* \* \* \* \*